United States Patent
Filo et al.

(10) Patent No.: US 7,599,506 B2
(45) Date of Patent: Oct. 6, 2009

(54) APPARATUS AND METHOD FOR BOOSTING SOUND IN A DENTA-MANDIBULAR SOUND-TRANSMITTING ENTERTAINMENT TOOTHBRUSH

(75) Inventors: Andrew S. Filo, Cupertino, CA (US); David G. Capper, Novato, CA (US)

(73) Assignee: Hasbro, Inc., Pawtucket, RI (US)

( * ) Notice: Subject to any disclaimer, the term of this patent is extended or adjusted under 35 U.S.C. 154(b) by 778 days.

(21) Appl. No.: 11/291,040

(22) Filed: Nov. 30, 2005

(65) Prior Publication Data

US 2006/0104456 A1   May 18, 2006

Related U.S. Application Data

(63) Continuation-in-part of application No. 09/513,656, filed on Feb. 25, 2000, now Pat. No. 7,120,509, and a continuation-in-part of application No. 09/626,187, filed on Jul. 28, 2000, now Pat. No. 6,801,815.

(60) Provisional application No. 60/154,602, filed on Sep. 17, 1999, provisional application No. 60/184,688, filed on Feb. 24, 2000, provisional application No. 60/634,398, filed on Dec. 8, 2004, provisional application No. 60/652,791, filed on Feb. 14, 2005.

(51) Int. Cl.
*H04R 25/00* (2006.01)
*A46B 9/04* (2006.01)

(52) U.S. Cl. .................. 381/151; 381/124; 15/167.1

(58) Field of Classification Search ............... 381/151, 381/124, 104, 107, 109; D04/108; 15/167.1, 15/105, 105.52, 106; 434/263
See application file for complete search history.

(56) References Cited

U.S. PATENT DOCUMENTS 4,341,230 A * 7/1982 Siahou ................ 434/263
5,331,707 A 7/1994 Irizarry (Continued)

OTHER PUBLICATIONS

PCT/US2005/43245—International Search Report. dated Nov. 30, 2006.

(Continued)

*Primary Examiner*—Xu Mei
(74) *Attorney, Agent, or Firm*—Perry Hoffman

(57) ABSTRACT

A device and method for transmitting sound waves between a signal source and a user's ears, wherein the sound waves bypass the air. The sound waves are conducted by the user's teeth and bones to the user's ears, where they are perceived as sound. Sound-transmitting toothbrushes and the like are described to transmit and/or conduct sound to the user's ear, while the user is brushing his or her teeth. The toothbrush head and a signal source are configured to produce sound waves for transmission through the toothbrush head to the user's mouth, and a tension controller is configured to control the volume of the sound waves based on the pressure applied by the toothbrush head. The signal source may produce sound waves directly or with the assistance of a transducer. The signal source may be replaceable, connect to a replaceable cartridge, or connect to an adaptor capable of downloading data to allow the signal source data to be replaceable. The tension controller may include gap spacing between the transducer coil and transducer plate. The tension controller may also include a boost switch configured as a bypass switch, activation signal, or force sensor.

49 Claims, 16 Drawing Sheets

U.S. PATENT DOCUMENTS

| | | | |
|---|---|---|---|
| 5,438,726 A | 8/1995 | Leite | |
| 5,572,762 A * | 11/1996 | Scheiner | 15/105 |
| 5,902,167 A | 5/1999 | Filo et al. | |
| 6,115,477 A | 9/2000 | Filo et al. | |
| 6,202,245 B1 * | 3/2001 | Khodadadi | 15/105 |
| 6,801,815 B1 | 10/2004 | Filo et al. | |
| 7,013,522 B2 | 3/2006 | Kumagai | |
| 7,418,757 B2 * | 9/2008 | Gatzerneyer et al. | 15/105 |

OTHER PUBLICATIONS

PCT/US2005/43245—Written Opinion of the International Searching Authority. dated Nov. 30, 2006.

PCT/US2005/43245—Notification of Transmittal of the International Search Report and the Written Opinion of the International Searching Authority or the Declaration. Nov. 30, 2006.

* cited by examiner

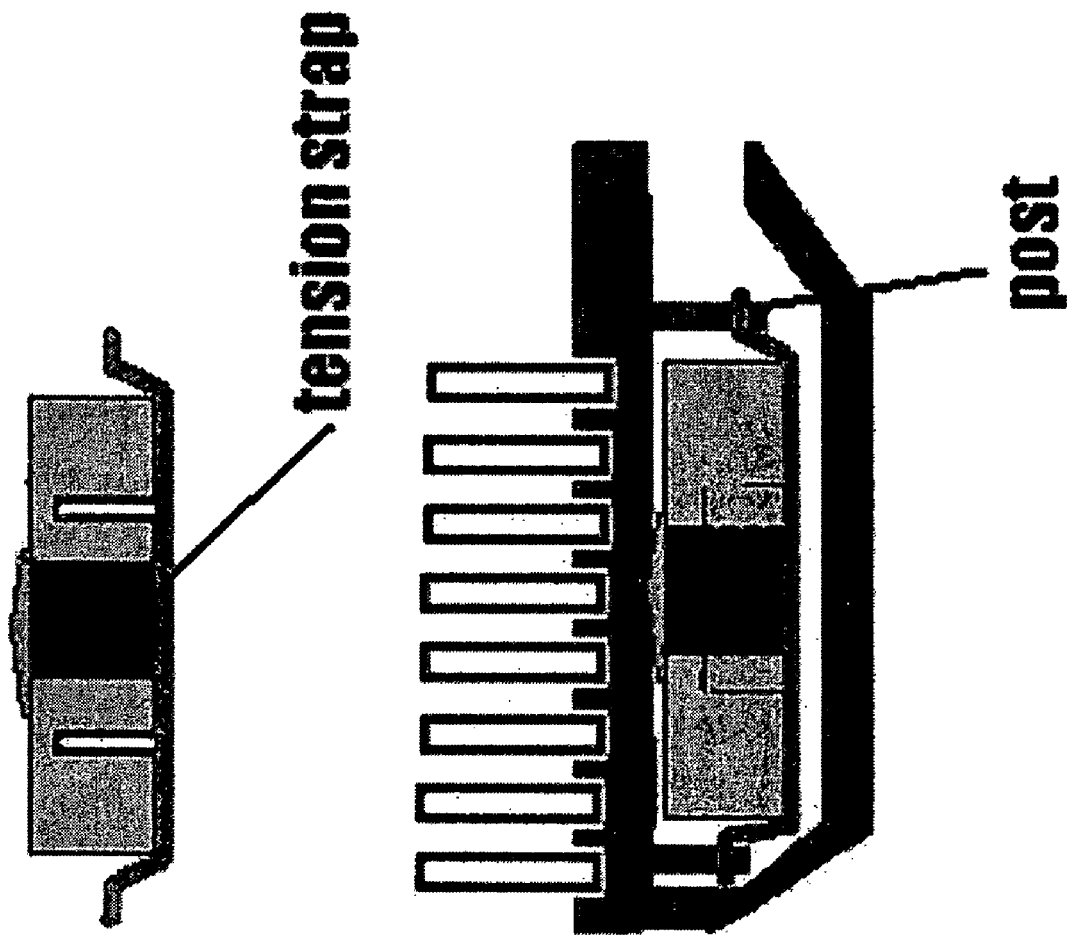

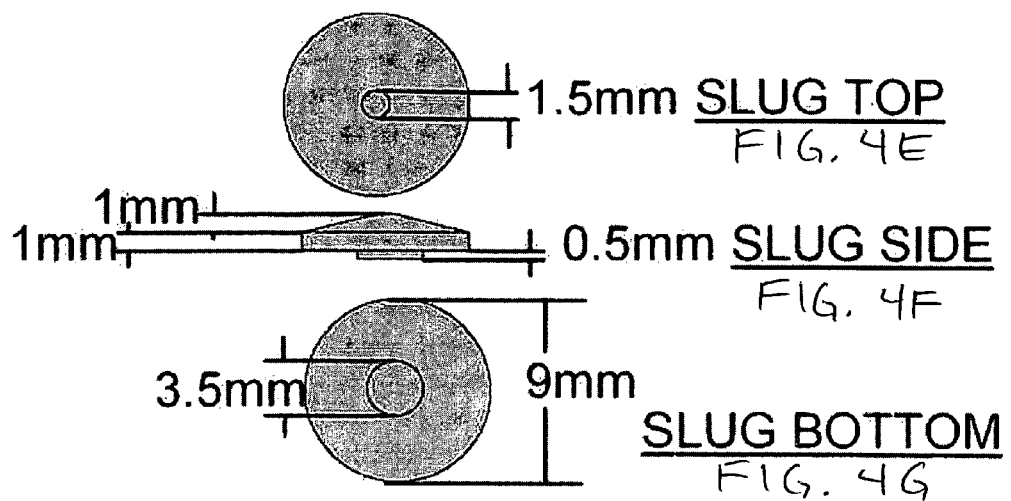
1.5mm SLUG TOP
FIG. 4E
1mm / 1mm / 0.5mm SLUG SIDE
FIG. 4F
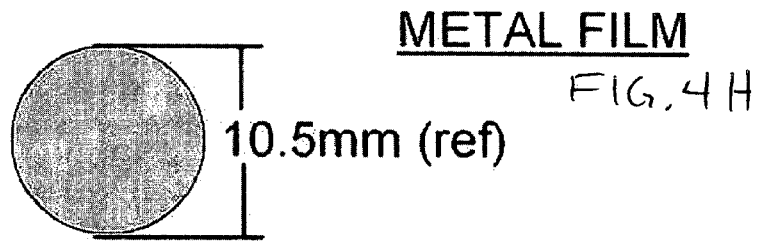
3.5mm / 9mm SLUG BOTTOM
FIG. 4G
METAL FILM
FIG. 4H
10.5mm (ref)
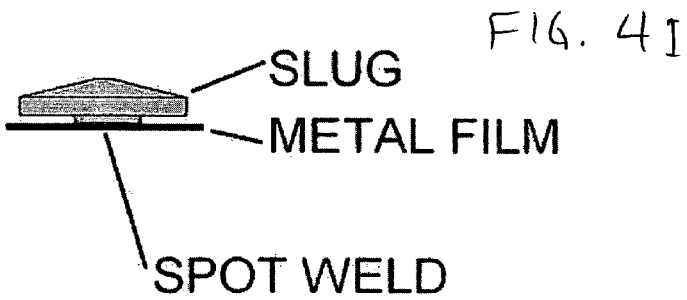
FIG. 4I
SLUG
METAL FILM
SPOT WELD
SLUG ASSEMBLY

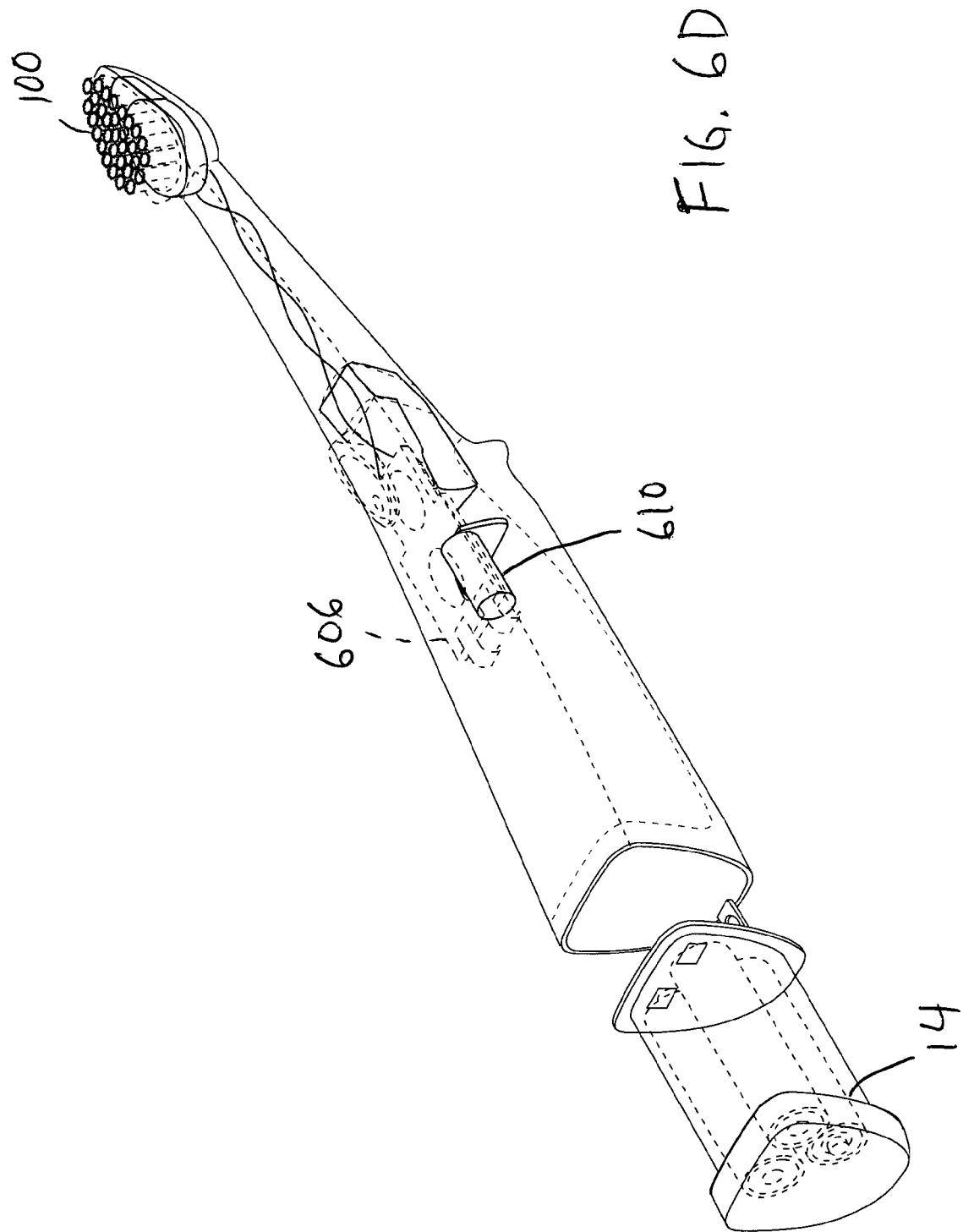

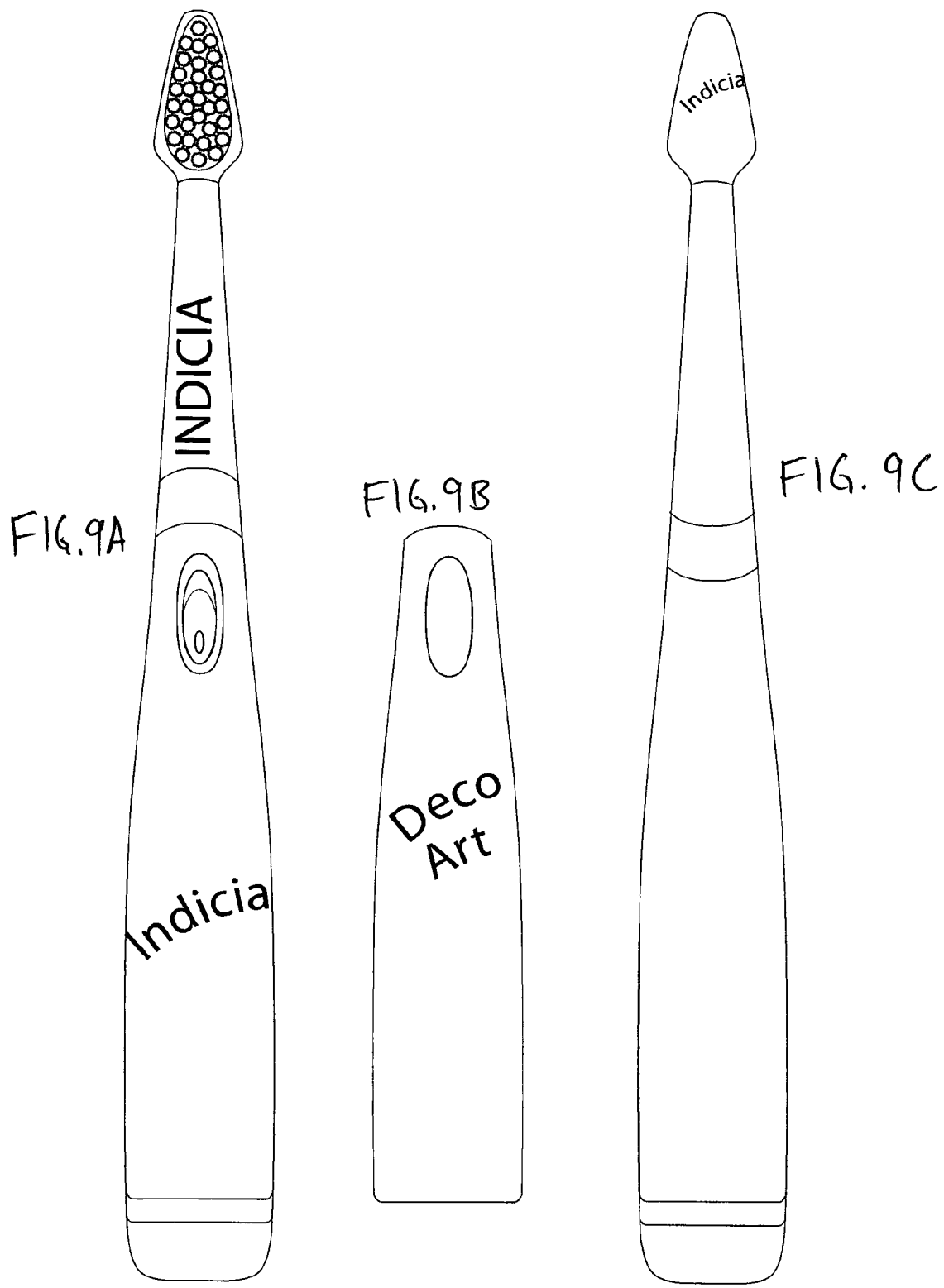

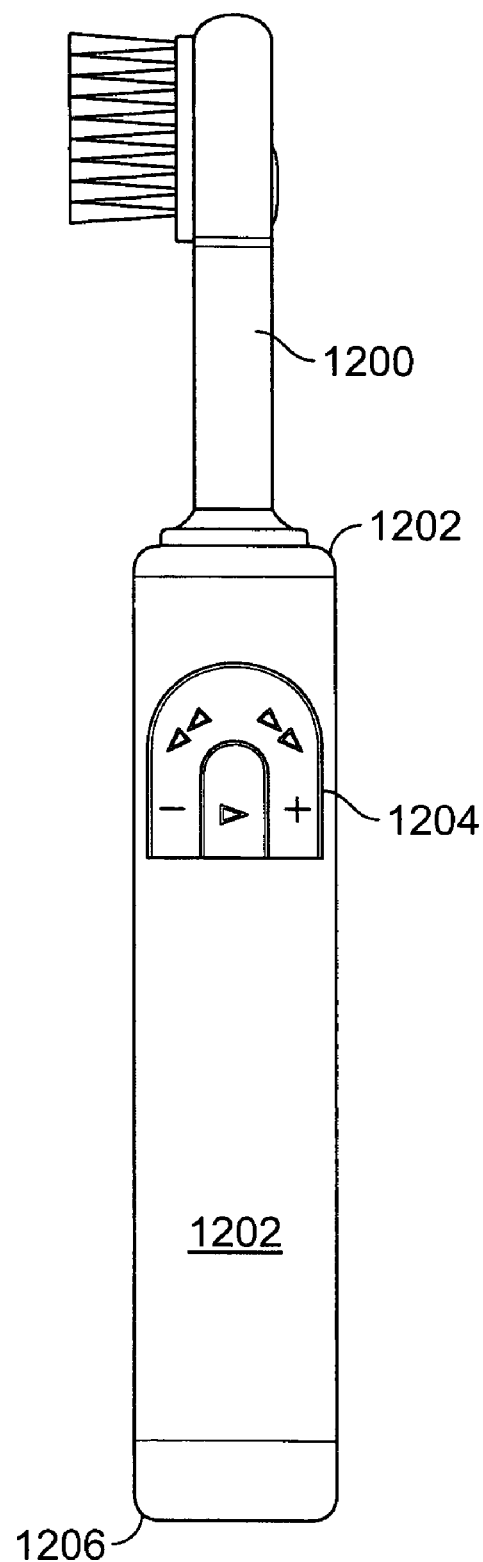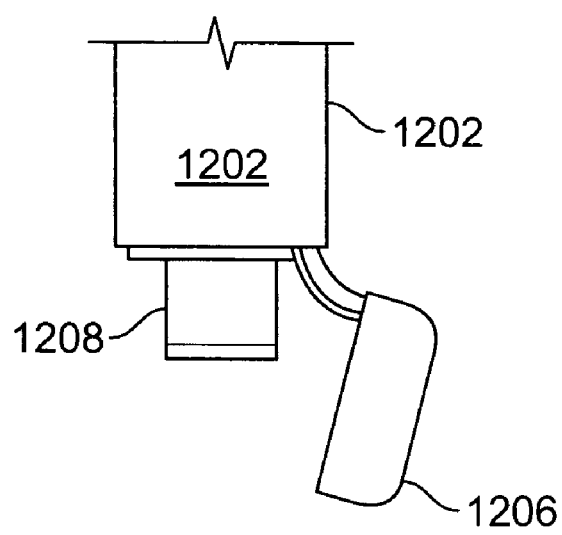
FIG. 12A
FIG. 12B

APPARATUS AND METHOD FOR BOOSTING SOUND IN A DENTA-MANDIBULAR SOUND-TRANSMITTING ENTERTAINMENT TOOTHBRUSH

CROSS-REFERENCE TO RELATED APPLICATION

This application is a continuation-in-part of U.S. patent application Ser. No. 09/513,656 filed Feb. 25, 2000 now U.S. Pat. No. 7,120,509 and Ser. No. 09/626,187 filed Jul. 28, 2000, which is Patented as U.S. Pat. No. 6,801,815, also claiming priority benefit pursuant to 35 U.S.C. 119(e) to U.S. Provisional Application Nos. 60/154,602 filed Sep. 17, 1999, 60/184,688 filed Feb. 24, 2000, 60/634,398 filed Dec. 8, 2004 and 60/652,791 filed Feb. 14, 2005 all prior applications being hereby specifically incorporated by reference in their entirety.

BACKGROUND OF THE INVENTION

1. Field of the Invention

The present invention relates generally to transmitting sound waves for entertainment via toothbrushes, and more particularly to apparatus and methods that modulate transmitted sound energy through a user's teeth and bone structure to the user's ears, e.g., proportional to brushing pressure.

2. Description of the Related Art

Mechanisms for transmitting sound to the ears that bypasses the air and external ears has been recently understood in the general denta-mandibular art. Through such mechanisms, sound waves are transmitted directly to the inner ears, without traveling through the air, by conduction through an object to bones in the user's head, from which the sound waves travel through the bones to the ears to be perceived as sound.

A particularly efficient way to incorporate this mechanism is through a process termed denta-mandibular conduction. Denta-mandibular conduction involves transmitting sound waves through the user's teeth and bones to the inner ear where it is perceived as sound. Because teeth are connected directly to bones in the head, they provide an advantageous non-airborne sound conduit to the ears.

Devices based on denta-mandibular sound transmitted are disclosed in several U.S. patents. As discussed in U.S. Pat. No. 5,902,167, herein incorporated by reference, an edible substance and a signal source are operatively associated and configured to produce sound waves for transmission through the edible substance to a user's mouth, from which sound waves are conducted by the user's teeth and bone structure to the user's ears to be perceived as sound. As further disclosed in U.S. Pat. No. 6,115,477, herein incorporated by reference, the sound-transmitting device may embody pacifiers, teething rings, pipes, cigarette holders, candy dispensers, toothbrushes, and toys.

It is not believed that a denta-mandibular device has used a method to boost or modulate the transmitted sound wave energy proportional to certain parameters such as the pressure applied to the user's teeth or the like. It would be desirable to incorporate this method into a toothbrush as to adjust the sound waves to facilitate good brushing technique. The invention described herein addresses this deficiency of the prior art.

SUMMARY OF THE INVENTION

The present invention provides a toothbrush capable of denta-mandibular sound transduction and also provides entertainment and tooth cleaning utility.

The denta-mandibular toothbrush contains a transducer which is mounted with a toothbrush head. The transducer provides controlled mechanical vibration energy to the head, in order to provide sound waves to the user's teeth and bones.

The toothbrush contains a signal source which may comprise a microchip having a preprogrammed song or message. The toothbrush is preferably sealed against moisture, and may include a replaceable head to allow for replacing worn out bristles or in order to change the sound source. The toothbrush may further include a motor to agitate the brush head to facilitate teeth cleaning.

In one embodiment, the toothbrush precisely controls the transducer gap and tension, such that the mechanical energy is efficiently coupled to the user's teeth in a range of approximately 60 to 120 grams of force.

In another embodiment, the toothbrush contains a pressure sensitive sensor and a "boost switch." The toothbrush precisely senses the pressure, such that the mechanical energy is efficiently coupled to the user's teeth in a range of approximately 40 to 100 grams of force. The boost switch acts to enhance the sound level or to modulate sound energy when proper brushing technique is applied. The boost switch may be implemented in a variety of ways, including a by-pass switch, an activation switch to provide a boost signal to the signal source, or as a force sensor.

By controlling the pressure applied to maximize the sound, the denta-mandibular toothbrush can act as an aid for developing proper brushing technique by providing audible sound when the pressure in the preferred range.

Additionally, the toothbrush may take on different embodiments in order to replace or add on to the signal source data. The toothbrush may make use of replaceable cartridges which contain signal source date. This would allow the user to change the sound he or she perceives while operating the device. Alternatively, the toothbrush may contain an adapter capable of uploading and downloading data, in order for new signal source data to be downloaded to the toothbrush. The toothbrush would contain a remote pad that would allow the user to cycle through the downloaded signal source data to select the sound he or she prefers while operating the device. These and other advantages are realized with the described embodiments. The invention advantages may be best understood from the following detailed description taken in conjunction with the drawing figures, and the accompanying Appendix A embodiments.

BRIEF DESCRIPTION OF THE DRAWINGS

The invention will now be more particularly described, by way of example only, with reference to the accompanying drawings, in which:

FIGS. 3A-F illustrate detailed views of the brush head transducer methods according to embodiments of the present invention;

FIGS. 4E-I illustrate the slug assembly according to a preferred embodiment of the present invention;

FIG. 6A illustrates the toothbrush assembly according to a preferred embodiment of the present invention incorporating the flexible bar assembly in a denta-mandibular toothbrush and FIGS. 6B-D illustrates a further alternative embodiment of the present invention which utilizes a motor to produce a reciprocating action at the brush head;

FIGS. 9A-C illustrates indicia bearing surfaces for toothbrush embodiments of the invention;

FIGS. 12A-B illustrate an alternative embodiment of the present invention in which the denta-mandibular toothbrush contains an adaptor capable of uploading and downloading data.

DETAILED DESCRIPTION OF PREFERRED EMBODIMENTS

The following description is provided to enable those skilled in the art to make and use the described embodiments set forth in the best modes contemplated for carrying out the invention. Various modifications, however, will remain readily apparent to those skilled in the art. Any and all such modifications, equivalents, and alternatives are intended to fall within the spirit and scope of the present invention.

In general, the present described embodiments relate to denta-mandibular sound-transmitting toothbrushes and the like that transmit and/or conduct sound to the user's ear, while the user is brushing his or her teeth. A toothbrush according to the present described embodiments generate mechanical energy in the bristles of the toothbrush that can be heard when the toothbrush is in use.

In an embodiment, while the user is brushing his or her teeth, the intensity of the sound is proportional to the pressure that the brush applies to the teeth. If too much or too little pressure is applied to the brush by the user, the user will perceive too little or no sound. Thus, the toothbrushes of the described embodiments encourage users to apply a moderate pressure, which facilitates good brushing technique.

One embodiment utilizes a miniature transducer that is capable of driving the toothbrush head with sufficient mechanical energy to be denta-mandibulary perceived by the user while brushing. In order to provide for the efficient production of mechanical energy, the transducer should produce minimal aerial sound. Typically, the toothbrush may produce approximately 95 dB of pressure at the bristles, while only leaking 50 dB of aerial sound.

Figure 1:
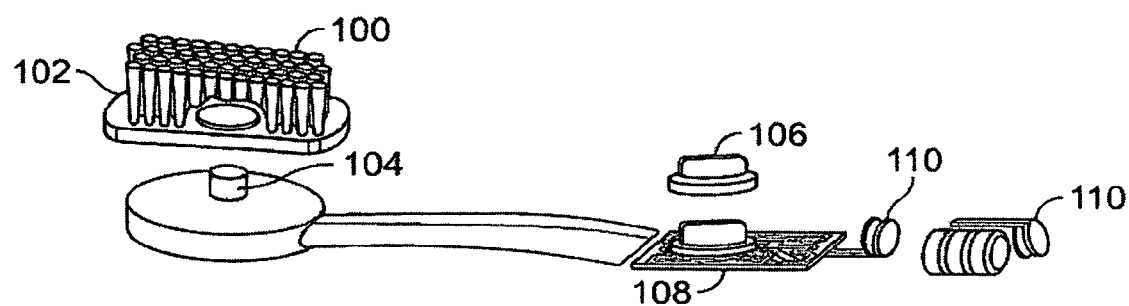
FIG. 1 shows the active components of one embodiment of the present invention.

FIG. 1 illustrates the active components of the denta-mandibular toothbrush of an embodiment of the present invention. The toothbrush includes a battery power source 112 and electrical contacts 110 to connect the battery source and a printed circuit board (PCB) 108. The PCB 108 includes the signal source data for driving the transducer with the desired sounds. Typical of such a signal source is the Winbond W561S15 chip that delivers 4 volts of Pulse Width Modulation (PWM) signal for audio applications. A push-button style switch 106 activates the signal source. The transducer comprises a coil assembly 104 and a metal plate or slug 102. The slug 102 is mounted to the brush head 100 having a platform with bristles. The coil assembly 104, when activated by the signal source located on the PCB 108, causes the slug 102 to vibrate, which in turn vibrates the platform and bristles locates on the brush head 100. The coil assembly 104 is typically 32 ohms, and if capable of producing up to 30 mGuass of magnetic field for mechanical deflection or motion. Such a construction allows sufficient mechanical energy to be transmitted through the bristles located on the brush head 100.

Figure 2:
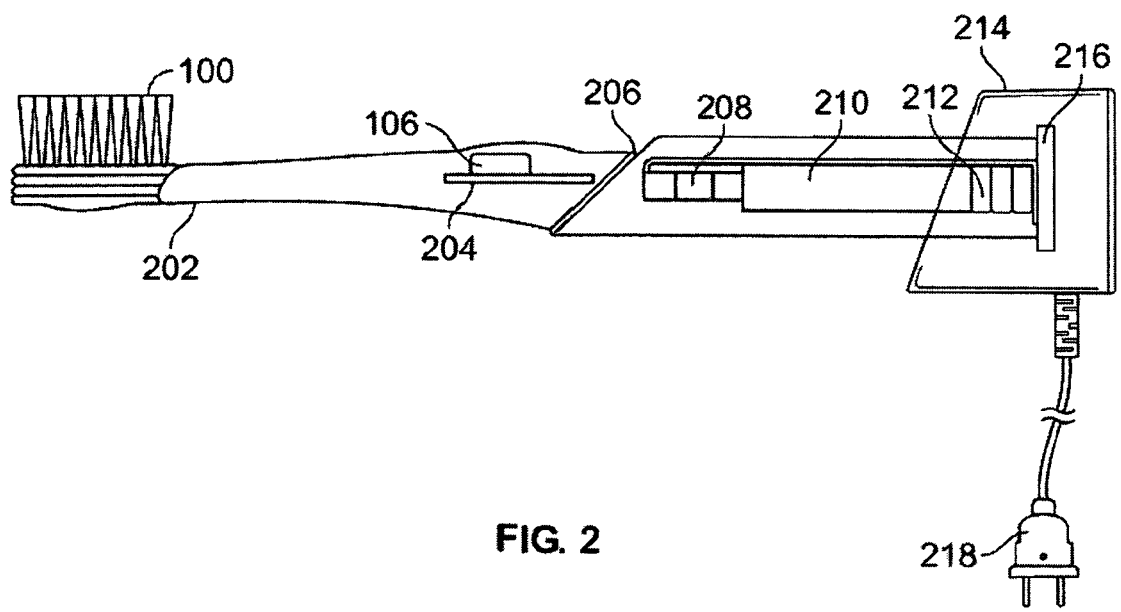
FIG. 2 is a diagram of the present invention, including a housing and base charger.

As illustrated by FIG. 2, the components of FIG. 1 may be mounted within a housing. A head and neck assembly 202 contains the push-button switch 106, the PCB 204, transducer and brush head 100. The head and neck assembly 202 is connected to the handle 208 via a joint 206. An O-ring type seal at the joint 206 is used to make the connection waterproof. The handle 208 contains a rechargeable battery 210 and a charging coil 212. The handle 208 may be placed into a charging base 214, containing a charging coil 216, and a 115 VAC plug 218. When the toothbrush is mounted in the charging base 214, the rechargeable battery 210 is charged via the charging coils 212 216. Additionally, the head and neck assembly 202 may be replaceable. For example, the head and neck assembly 202 may be replaced when the bristles are worn down, or alternatively in order to change the sounds that are generated by the signal source.

FIGS. 3A-F illustrate detailed views of an embodiment of the brush head 100, and particularly the brush head preloading methods according to the described embodiments. The transducer is mounted integral to the neck 314, and includes a coil 310, a core 308, a back plate 316, and a magnet 306. A wire 312 connects the transducer to the PCB 204. A transducer plate or "slug" 310 is mounted to the brush head platform 302. The brush head platform 302 contains a plurality of standard toothbrush bristles 300. The brush head platform 302 is attached to the neck 314 via a bellows assembly 304. This bellows assembly 304 correctly spaces the gap between the slug 310 and the coil 310, and also allows the brush head platform 302 to vibrate, while still providing a waterproof seal for the transducer.

Figure 3A:
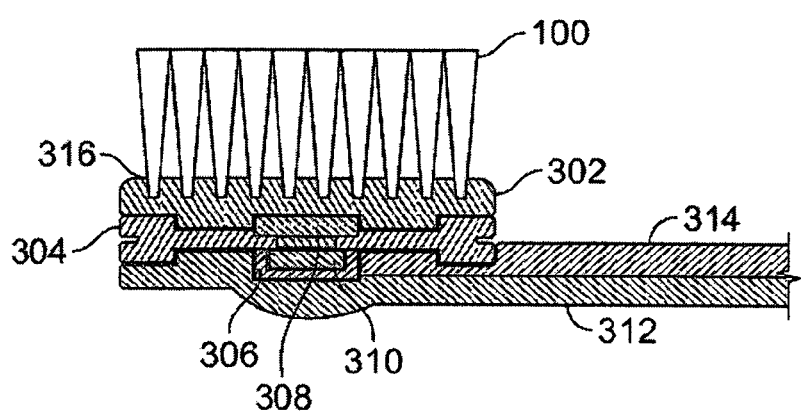
Figure 3B:
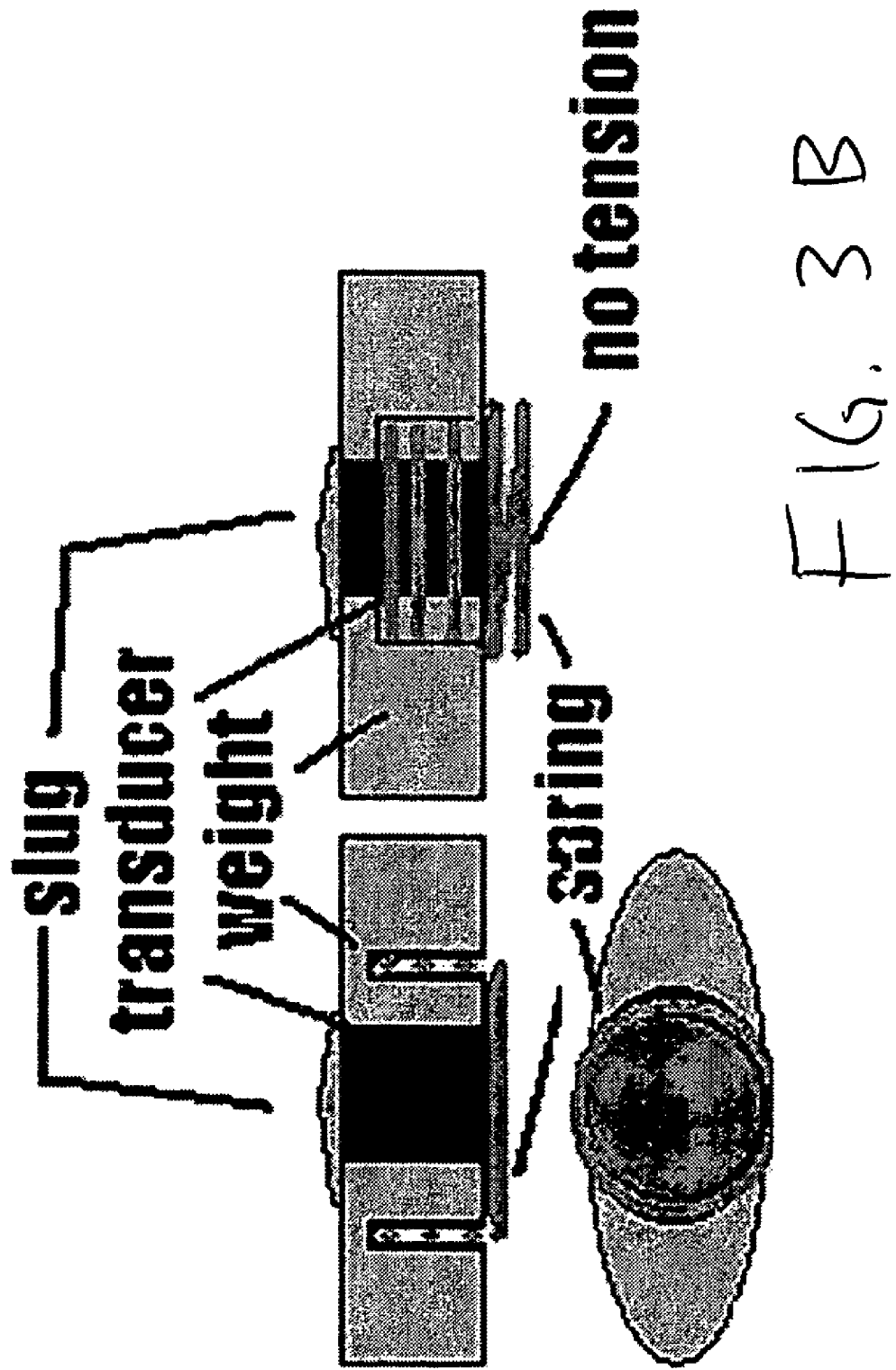
Figure 3E:
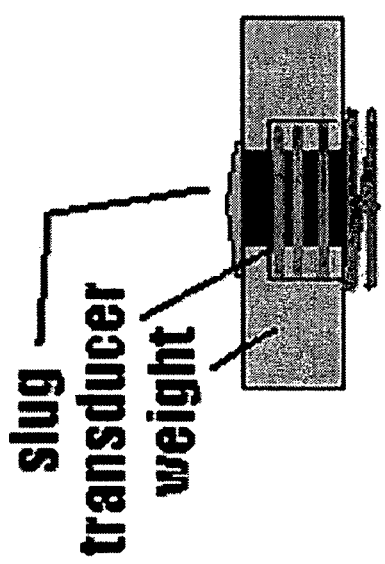
Figure 3F:
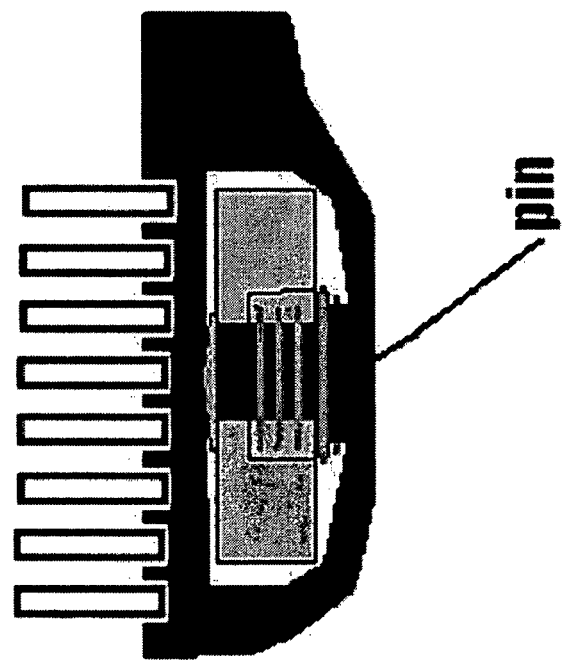

FIGS. 3B-F illustrate detailed views of the brush head transducer methods according to embodiment for respective self-centering linear coil, spring loading, and tension strap preloading methods facilitating sound transfer via the toothbrush bristles of the toothbrush head assembly 100. In addition to the bellows assembly 304 as illustrated in FIG. 3A, there are several methods of controlling the tension and gap within the transducer. FIG. 3B shows the slug 310 of the transducer, weight and spring assemblies. The bottom view of the assembly of FIG. 3B shows a dome-shaped pressure plate opposite the slug 310 for spring pressure. As shown and described, the transducer is pre-loaded at the bristle plate to ensure that the maximum vibration is sent to the bristles, which has been found to achieve transmission at about 120 grams of loading force to facilitate coupling. The loading mechanism will also permit low frequency vibration sound production. As illustrated in FIGS. 3C-F this may be accomplished by using a flexible means, such as the spring coil or dome spring, a domed rubber cap, or the like such as that found in a keyboard or a strap or the like. In order for the transducer to function properly, the amount of tension should be controlled. The transducer configuration must control the positioning of the slug relative to the electromagnetic coil such that the mechanical energy is efficiently coupled to the user's teeth in a range of between approximately 40 to 100 grams of force. Any less force is ineffective for teeth cleaning, and any more is too great a force. By controlling the pressure applied to maximize the sounds, the denta-mandibular toothbrush can act as an aid for developing proper brushing technique by providing an audible sound when the pressure is in the preferred range.

Figure 4A:
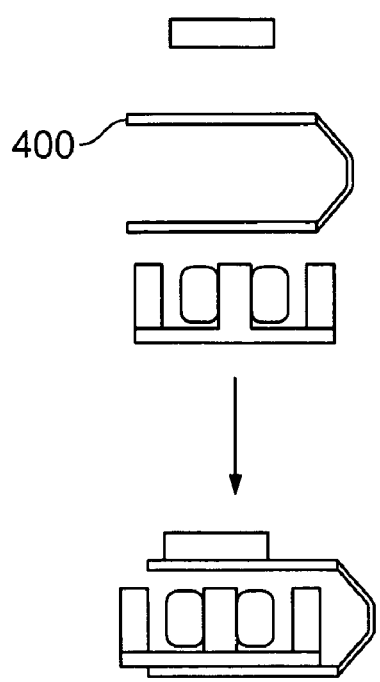
FIGS. 4A-D illustrate several designs to control the tension and slug assembly of the electromechanical transducer.
Figure 4B:
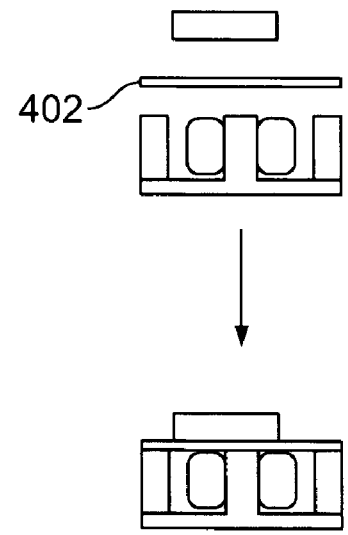
Figure 4C:
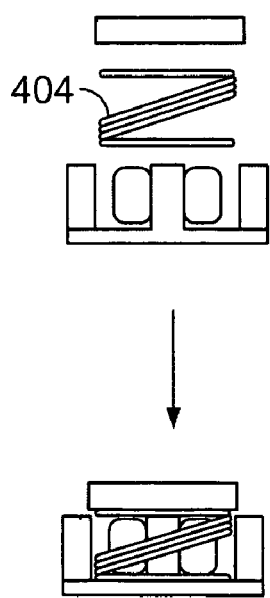
Figure 4D:
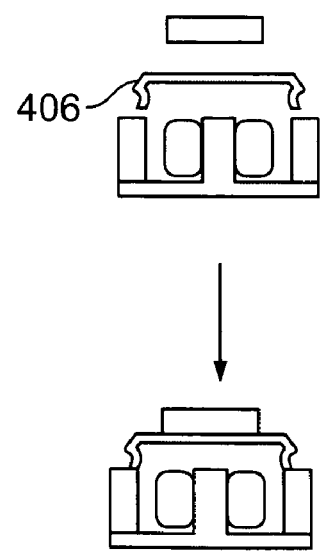

Various transducer methods may be employed as illustrated in FIGS. 4A-I. FIGS. 4A-D illustrate several designs to control the tension and slug assembly of the electro-mechanical transducer, showing transducer gap and tension techniques in exploded and assembled views. FIGS. 4E-I illustrate the slug assembly according to a preferred embodiment. In FIG. 4A the transducer gap and tension control of slug assembly of the electromechanical transducer of item 400 illustrates a torsion bar attached to a base of the coil and to the slug that may be used to accurately control the gap spacing between the coil and the slug. In FIG. 4B the transducer gap and tension control of slug assembly of the electromechanical transducer of item 402 illustrates a diaphragm that may be used as shown to accurately control the gap spacing between the coil and the slug. In FIG. 4C the transducer gap and tension control of slug assembly of the electro-mechanical transducer of item 404 illustrates a spring (preferably either coated or non-metallic) which can be mounted between the coil and slug. In FIG. 4D the transducer gap and tension control of slug assembly of the electromechanical transducer of item 406 illustrates the aforementioned bellows assembly to accurately control the gap spacing between the coil and the slug. In FIGS. 4E-I the slug assembly is illustrated showing top, side and bottom views, and a spot weld interface between the slug and the metal film of the slug assembly. The shape of the slug is a cone, where the point of the cone would touch the bristle plate, with the mass of the slug of about 2.5 grams in the present described embodiment.

Figure 5A:
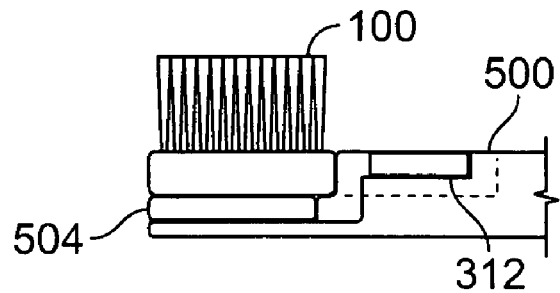
FIGS. 5A-D illustrate alternative embodiments of the brush head design, with FIG. 5D illustrating the toothbrush transducer head assembly according to a preferred embodiment of the present invention incorporating the slug assembly according to FIGS. 4E-I.
Figure 5B:
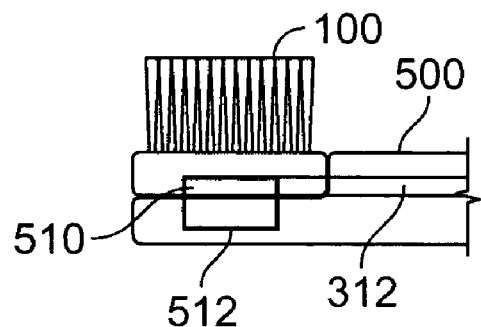
Figure 5C:
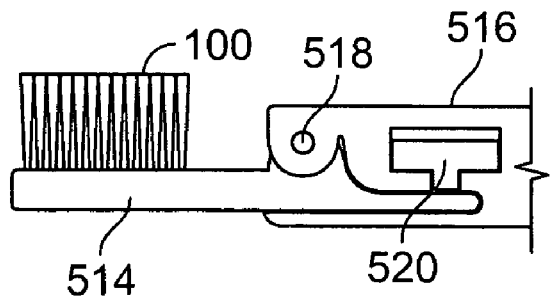

As described above, the transducer is generally formed using an electromagnetic coil in the neck of the toothbrush, and a slug mounted to a platform of the brush head. However, the transducer may be formed as illustrated in FIGS. 5A-D. FIG. 5A illustrates that the transducer may be formed using a piezo-electric crystal 504 to generate the mechanical vibration. In construction, the piezo-electric crystal 504 may be sandwiched between the neck 500 and the brush head 501. FIG. 5B illustrates the positioning of the coil 510 and the slug 512 may be reversed as compared to the embodiment presented in FIG. 3A, i.e. the slug 512 may be mounted in the neck 506, and the coil 510 in the brush head 507. Alternatively, as illustrated in FIG. 5C, the transducer may be positioned away from the brush as shown. The transducer 520 may be mounted in a handle 516 and in contact with a mechanical lever-pivot configuration 518. As the transducer vibrates, the mechanical energy is transmitted to the brush heard 514 via the pivoting action of the lever 518.

Figure 5D:
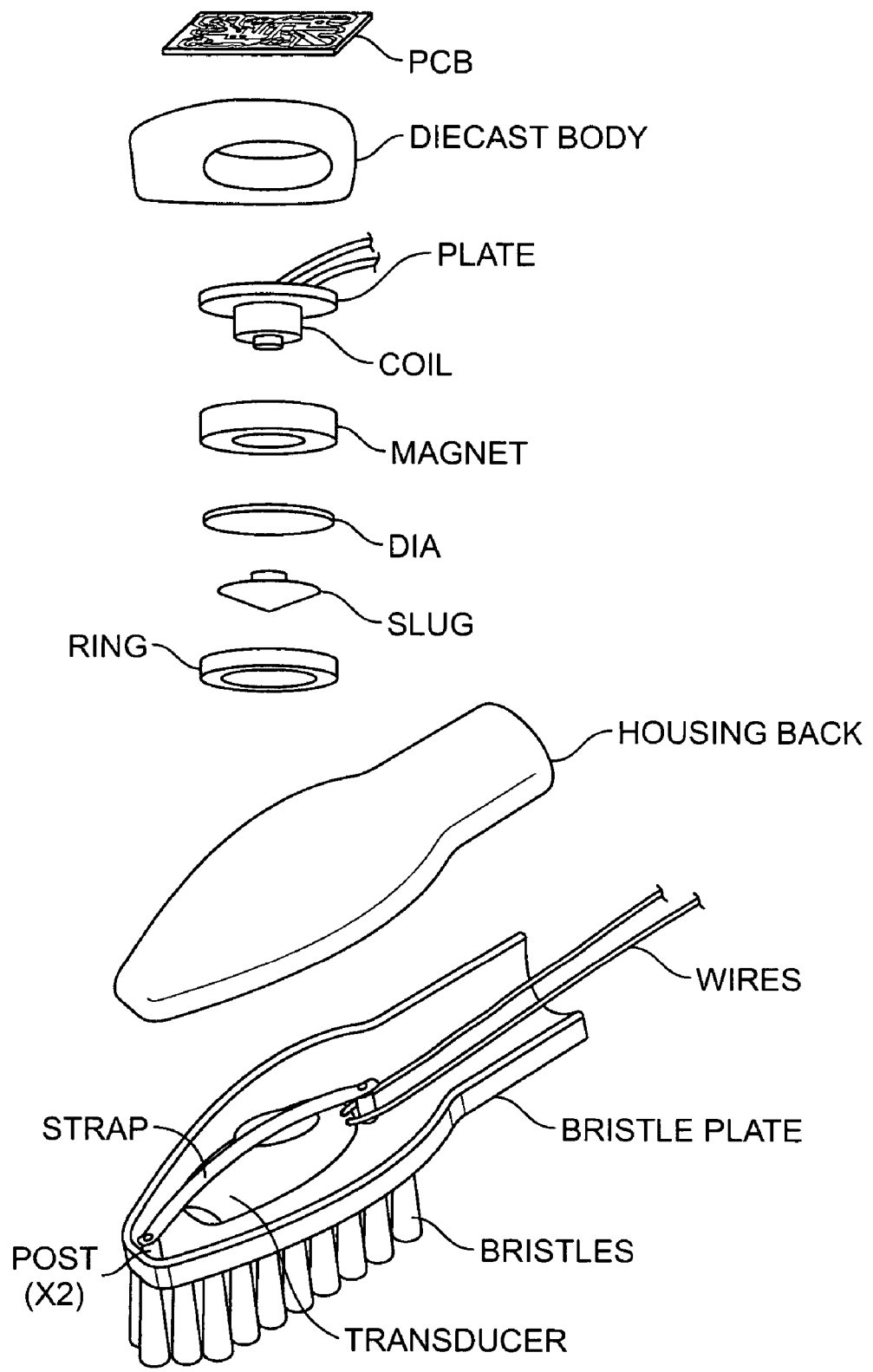

Alternatively, the transducer 520 may further provide its transducer as operatively associated with the signal source to produce vibrations for aerial sound from the signals operatively associated for sound transmission with the transducer to which the transducer can transmit vibrations in the user's mouth, where the sound-transmitting element is positioned adjacent to the transducer so that vibrations transmitted from the signal source to the sound-transmitting element are sufficient to be perceivable by the user as sound when the sound-transmitting element is in contact with the user's non-conductive tissue. This facilitates sound production allowing the user to continue to hear sound signals. In FIG. 5D, the transducer has a body with added mass of about 2 to 3 grams.

FIG. 5D illustrates the toothbrush transducer head assembly according to a preferred embodiment incorporating the slug assembly according to FIGS. 4E-I above.

In FIG. 5D, the transducer having the body with added mass of about 2 to 3 grams provides low frequency wave production this is perceived by the user as bass. Bass starting at 250 Hz is best heard while brushing. The transducer includes a ring which holds the diaphragm to the body, with the slug welded to the diaphragm. The assembly magnet, coil and plate generate the magnetic force to deflect the diaphragm, and the body creates inertial mass for low frequency vibration and serves as an armature for the assembly. A PCB on the back provides a means for wire attachment. As described, the head assembly including the transducer is held to the bristle plate by a strap fixed, e.g., by two posts on the bristle plate. The housing back is welded to the bristle plate to ensure a watertight seal. The slug of the transducer is pressed against the back of the bristle plate to transfer vibrations to the bristles and ultimately the user's teeth.

Figure 6A:
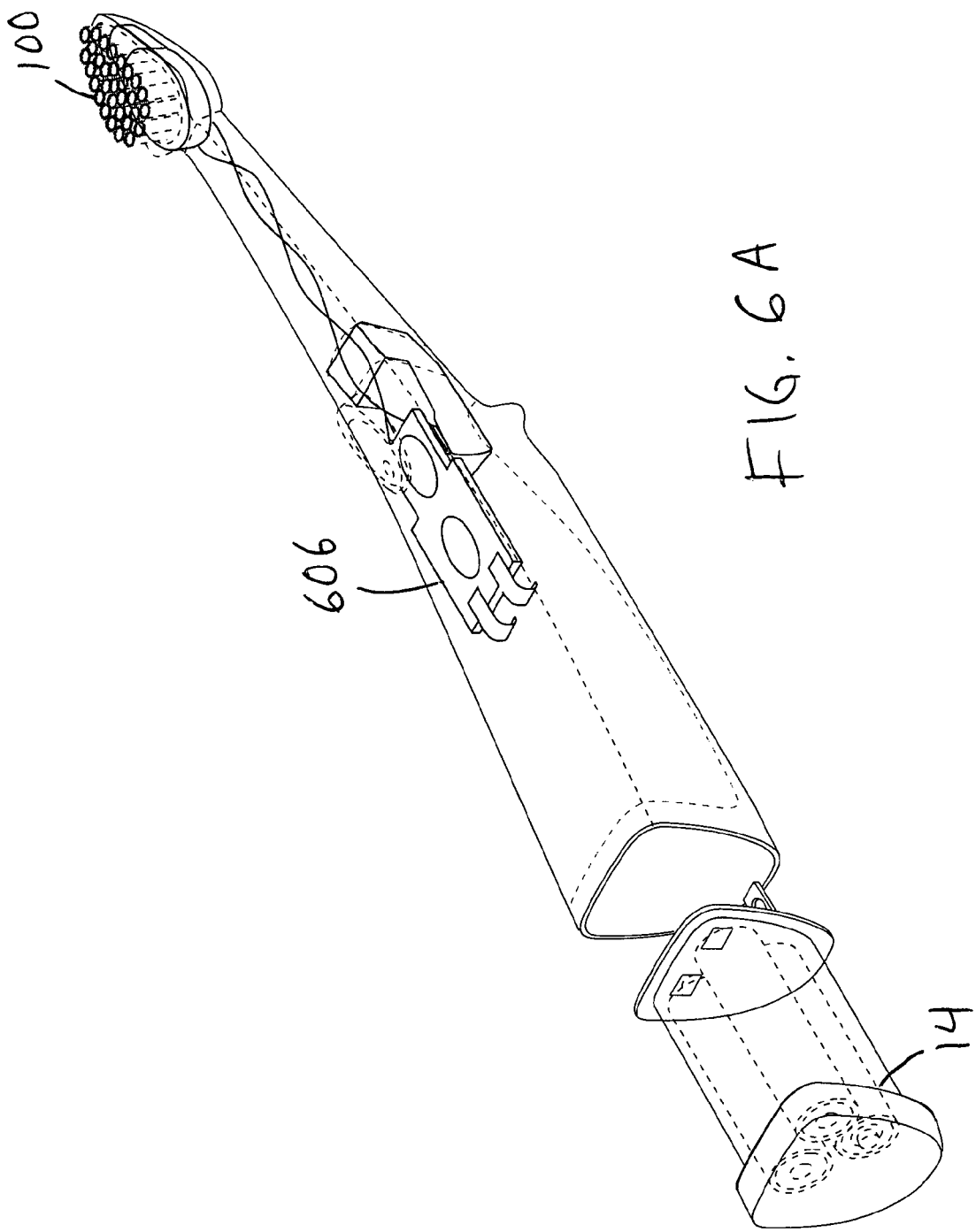
Figure 6C:
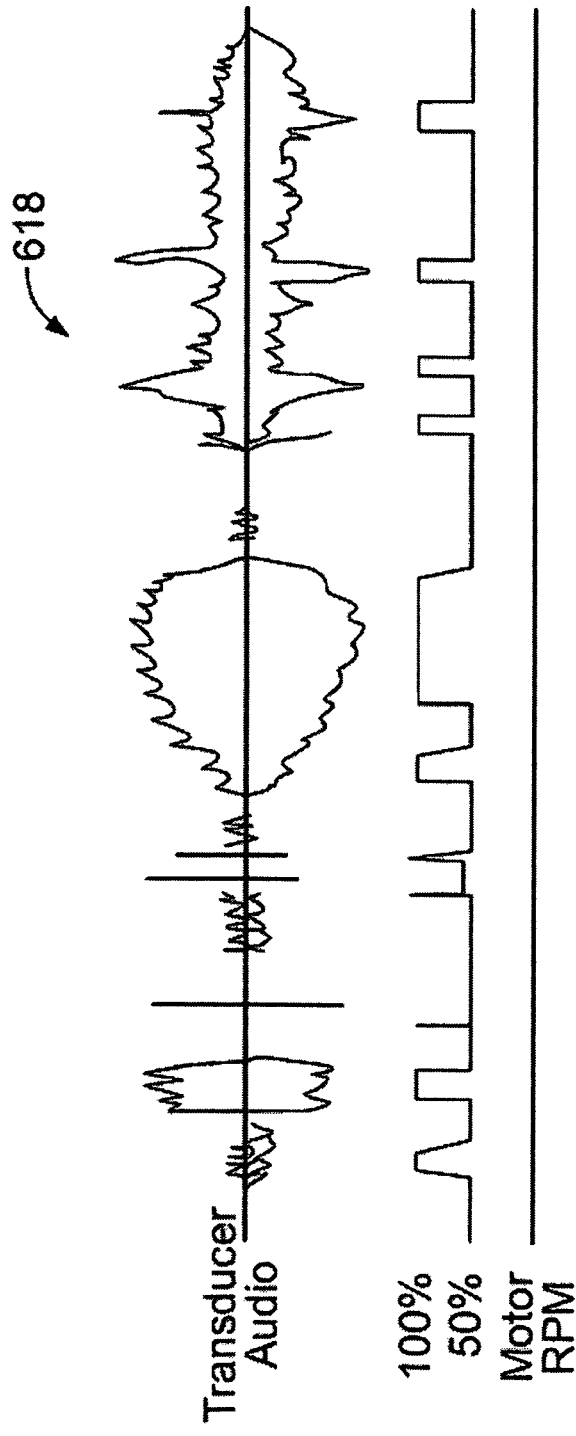
Figure 6B:
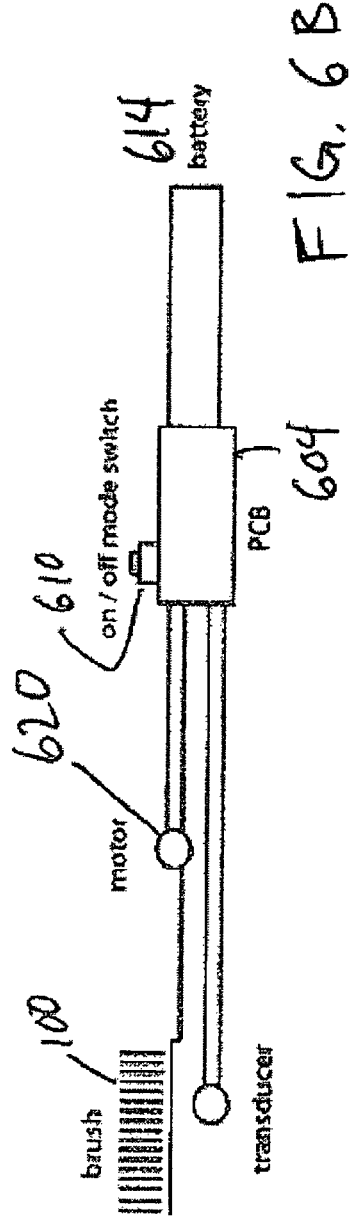

FIG. 6A illustrates the toothbrush assembly according to a preferred embodiment incorporating the flexible bar assembly 602 in the denta-mandibular toothbrush operable with PCB 604. When pressure is applied at the brush head 100 causes the flex bar assembly 602 to bend. PCB 604 supports an underside boost switch 606 with a chip-on-board 608, and On/Off switch 610 being operated from an over molded front recess/switch push-button 612, discussed further in connection with FIGS. 10A-C concerning over mold front recess and rear landing gear/finger guard features. The PCB 604 is positioned for electrical coupling with the battery assembly 614 as illustrated. FIGS. 6B-D illustrate a further alternative embodiment that utilizes a motor 620 to produce a reciprocating action at the brush head 100. FIG. 6D illustrates an alternative embodiment wherein in addition to the features previously discussed, the toothbrush includes a motor 610, a gearbox 612, and a grip handle 608 that cooperate to produce a reciprocating action at the brush head 100. Such an embodiment can be used to increase the brushing effectiveness of the denta-mandibular toothbrush. The control chip of the PCB 604 may control the speed, direction, and duration of the motor's 610 operation to further increase the motor's 610 effectiveness. Thus the flexible joint at the flexible bar assembly 602 can be used in conjunction with the boost switch 606. The body and neck are connected by a flex joint, and the boost switch 606 is depressed by an activation via the neck. The boost switch 606 is pinched between the body and neck while pressure is applied to the brush head 100. The boost switch 606, the on/off switch 610, and battery source 614 are interconnected with the PCB 604. As described, the transducer is mounted behind the bristles. As shown, the hinge in the neck activates the boost switch when the user presses the unit up against their teeth, with the switch 610 in the front and finger rest provided with a soft over mold in the back. A boost switch button may be located on the body and depresses the boost switch 606. The boost switch thus may be provided separately as a manually activated switch by the user and may also incorporate a soft over mold if desired.

FIG. 6A further illustrates that the flexible bar boost switch construction may provide the flex bar as a molded as part of the neck 1008. A flex bar lock secures the flex bar to the neck of the toothbrush. A flex joint/seal/button is trapped and compressed between the neck and the body of the toothbrush. This serves as a movable joint, button cap, and body seal. The boost switch 606 and the PCB 604 are positioned at the flex bar. Signals from the PCB 604 are conducted to the transducer via wires. The sound pressure from the transducer is conducted through the seal/transmission plate and through the brush head 100.

By adding the small motor 610 with an eccentric weight 616 it is possible to produce additional low frequency vibration effects for the entertainment of the user. The pattern 618 of these vibrations can be controlled and synchronized and modulated by the music chip on the PCB. The magnitude of these vibrations can be made great enough to also provide cleaning benefits to the user's teeth.

Figure 7A:
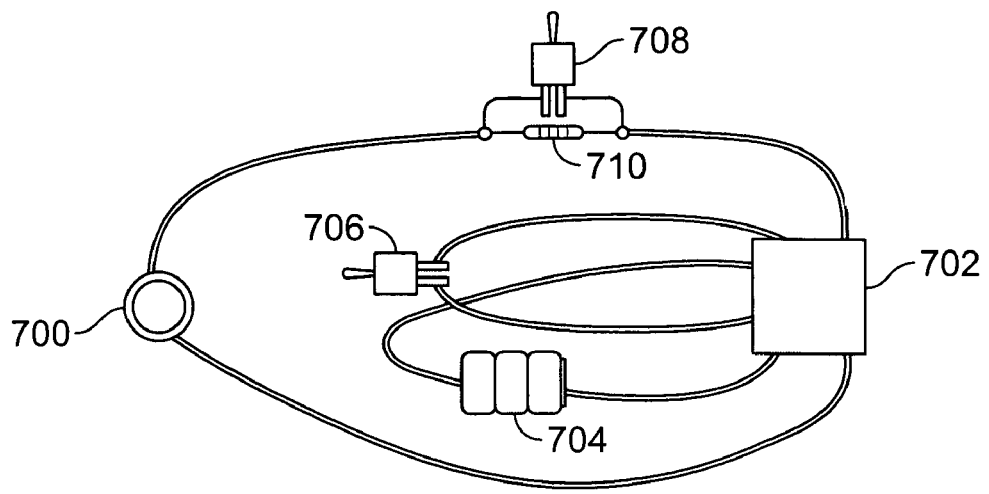
FIGS. 7A-C illustrate schematic diagrams of different methods for controlling the volume level in a denta-mandibular tooth brush.

In other embodiments the boost switch may be physically implemented in different ways to accomplish the sound boosting feature. In one embodiment, the boost switch may be implemented using a by-pass switch. FIG. 7A is a schematic diagram of the bypass switch as it relates to other components of the described embodiments. A limiting resistor, e.g., of 100 ohms, resistor 710 is in series with the transducer 700 and the PCB 702, suppressing the sound pressure produced by the transducer 700. A bypass switch 708 is placed in parallel with the limiting resistor 710 of 100 ohms. When the bypass switch 708 is activated it effectively shorts out the limiting resistor 710 of 100 ohms, thereby allowing for maximum sound production. Additionally FIG. 7A illustrates the connections between the on/off switch 706 and the PCB 702 and the battery source 704 and the PCB 702.

Figure 7B:
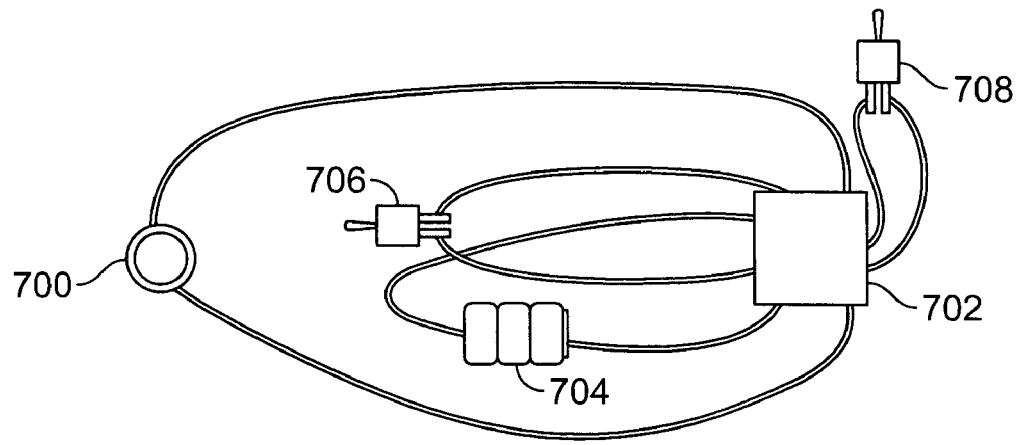

FIG. 7B illustrates another embodiment in which an activation signal is provided by the boost switch 708 to the signal source on the PCB 702. The data from the boost switch 708 can be used to trigger volume levels on the PCB 702, as well as other function such as timers and continuous use detection in order to measure the duration and technique of brushing. Additionally FIG. 7B illustrates the connections between the on/off switch 706 and the PCB 702, the battery source 704 and the PCB 702, and the transducer 700 and the PCB 702.

Figure 7C:
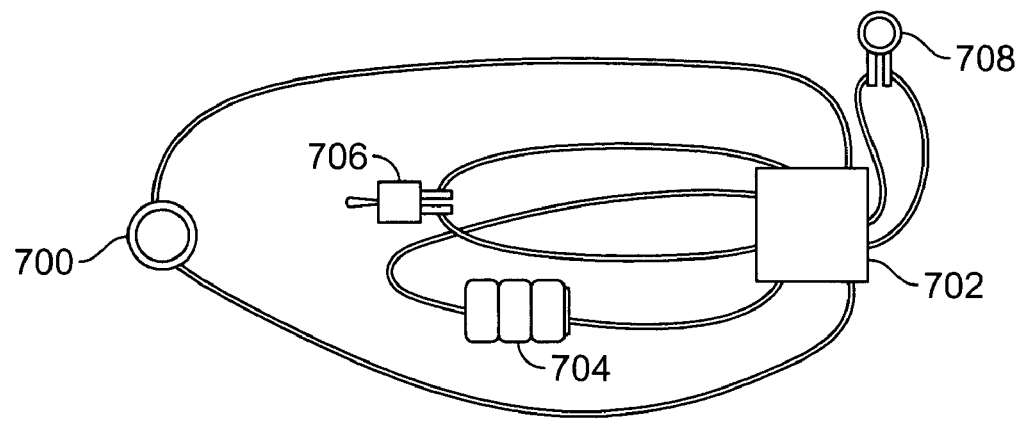

FIG. 7C illustrates another embodiment where the boost switch is implemented as a force sensor 708 such as an Interlink Electronics Force sensing Resistor FRS #0004. This device produces an analog signal proportional to the pressure applied to it. The PCB 702 can measure this pressure signal and respond to the user to indicate if too much pressure or too little pressure is being applied to the brush by the user. Additionally FIG. 7C illustrates the connections between the on/off switch 706 and the PCB 702, the battery source 704 and the PCB 702, and the transducer 700 and the PCB 702.

Figure 8A:
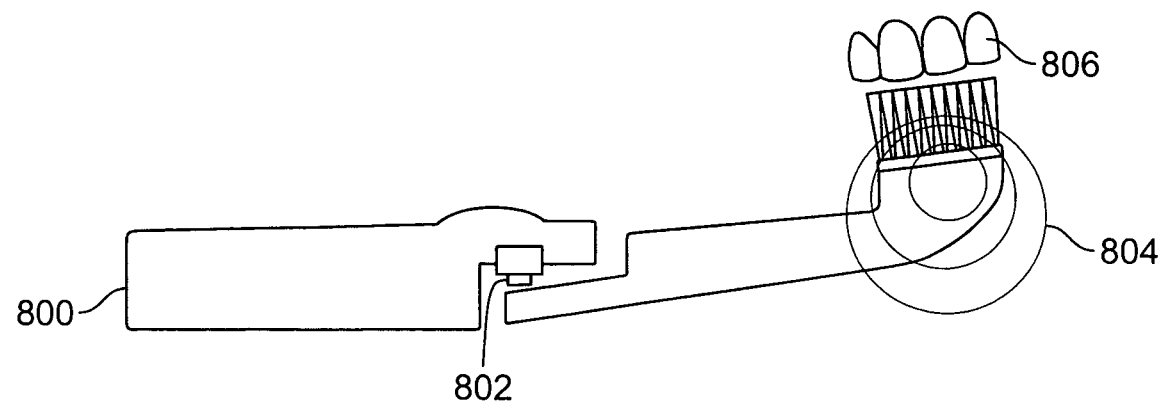
FIGS. 8A-C illustrate how the denta-mandibular boost switch controls sound pressure in response to force applied to the brush head by employing the flexible joint and boost switch according to one embodiment of the present invention.
Figure 8B:
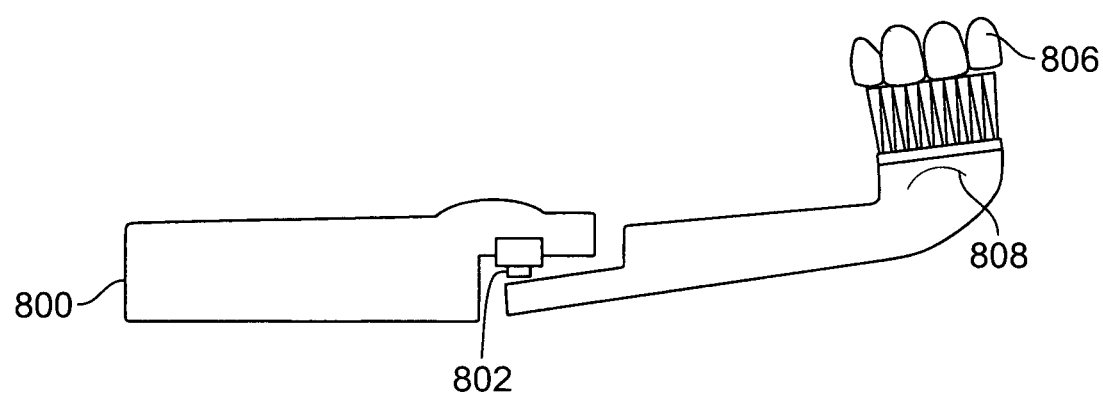
Figure 8C:
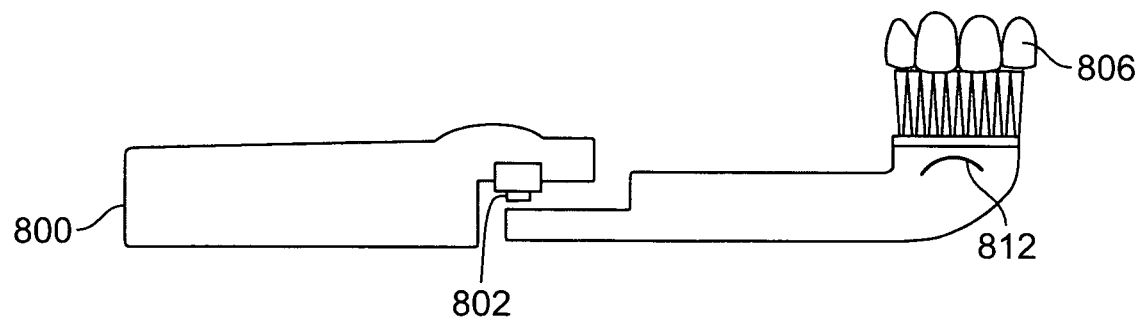

FIGS. 8A-C illustrate how the denta-mandibular boost switch controls sound in response to force applied to the brush head by employing the flexible joint and boost switch. The figures illustrate the manner in which the boost switch may be activated with respect to handle 800. When no pressure is applied to the user's teeth 806 by the device, as shown in FIG. 8A, a slight sound 804 may be perceived by the user, indicating the signal source is on and operating and the boost switch remains open 802. As shown in FIG. 8B, once contact is made with the user's teeth 806 at 10-20 grams of force, sound 808 is perceived through the denta-mandibular sound transmitting process at a volume, e.g., nearly 20 dB louder. Additionally the force applied is not enough to depress the boost switch 802. As more pressure is applied to the user's teeth 806, as shown in FIG. 8C, the boost switch 810 is depressed. Specifically, the boost switch 810 is depressed when the force applied to the user's teeth 806 is approximately 40 grams. The level of increase in perceived volume is exaggerated by the boost switch 810 to produce a much louder sound 812. The volume increase is nearly 20 dB more than the volume when minimal pressure is applied as in FIG. 8B.

Figure 10A:
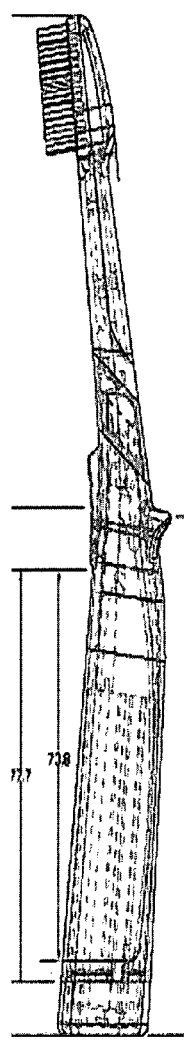
FIGS. 10A-C are side views of toothbrush embodiments illustrating toothbrush handles including over mold features for the front recess/switch push-button, and rear landing gear/finger guard.
Figure 10B:
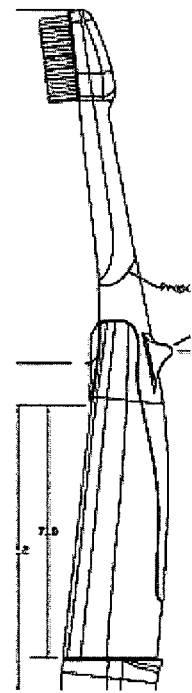
Figure 10C:

FIGS. 9A-C illustrates indicia bearing surfaces for toothbrush embodiments, and FIGS. 10A-C are side views of toothbrush embodiments illustrating toothbrush handles including over mold features for the front recess/switch push-button 1002, and rear landing gear/finger guard 1004. Decorative artwork may be provided as a label, e.g., Deco Art 900 in FIG. 9B positionable at the toothbrush handle 902, or other indicia or the like may be provided directly at handle 902, neck 904 (FIG. 9A), or at the back portion of the toothbrush head for carrying indicia 906 (FIG. 9C). FIGS. 10A-C side views show the toothbrush handles including over mold features at the front recess/switch push-button 1002, and rear landing gear/finger guard 1004. The described embodiment of the brush shape allows for a multiple of considerations. The body is triangular to permit comfortable holding by youth and adult hands. A recessed switch is provided to prevent accidental operation of the switch on the body. Also on the body is a thumb break and finger guard that conforms the user's hand for proper holding. The body length is appropriate for comfortable holding, and the finger guard doubles as a perch so the brush can horizontal positioned. The flat face of the body permits easy decoration, which may contain such information as music artist picture and song name indicia.

Figure 11B:
FIGS. 11A-B illustrate an alternative embodiment of the present invention which allows removable cartridges containing signal source data to be used by the denta-mandibular toothbrush.
Figure 11A:
Figure 11C:
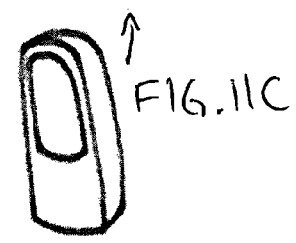

FIGS. 11A-B illustrate an alternative embodiment that accommodates removable cartridges containing signal source data to be used by the denta-mandibular toothbrush. As illustrated in FIGS. 11A-B, the embodiments may include a removable cartridge 1104. In this embodiment, the removable cartridge 1104 may contain the PCB itself or data to be transferred to the PCB once the removable cartridge 1104 is inserted into the toothbrush 1100, e.g., at bottom handle portion 1102. The removable cartridge 1104 may contain signal source data so that each removable cartridge 1104 contains a unique collection of songs or verbal instructions. The image 1106 on the removable cartridge 1104 indicates to the user the signal source data that is on the removable cartridge 1104. Various embodiments are contemplated in connection with the removable component architecture. To this end, components such as the removable cartridge 1104 may be provided for additional content, media or functionality; alternately, the neck and brush head assembly of the toothbrush 1100 also may be provided as a modular component. The brush body 1102 in its most basic form may be provided to include simply the batteries and controls, and optionally a motor as discussed herein if desired. With the brush body 1102 including therein only batteries and controls, in its most basic form, a combination other components may be introduced as external modules. The brush body 1102 may include additional components, e.g., including digital memory and/or computer integrated circuit devices as the removable cartridge 1104. The transducer component in the neck and brush head assembly of the toothbrush 1100 also may be provided as a separate removable modular component. Additionally the computer and memory maybe provided either as separate components or in a single integrated circuit, for instance a speech chip or the like such as a single chip controller for providing a sound and speech processing. The transducer, digital memory and/or computer integrated circuit devices alternately may be provided as part of the neck and brush head assembly of the toothbrush 1100 as a separate external modular component.

FIGS. 12A-B illustrates an alternative embodiment in which the denta-mandibular toothbrush contains an adaptor capable of uploading and downloading data. Herein the toothbrush is provided with an adaptor capable of uploading and downloading data such as an USB adaptor. The adaptor 1208 is connected to the PCB and is located at the bottom of the body 1202. A cap 1206 covers the adaptor 1208 as to give the toothbrush a uniform look and to protect the adaptor 1208 when it is not in use. The adaptor 1208 allows the PCB to download signal source data to be stored onto the PCB memory. There is a remote pad 1204 located on the toothbrush body 1202 that allows the user to cycle through the downloaded signal source data to select the sound to be transmitted through the neck and brush head 1200.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A device to communicate sound to a user by the transmission of signals through the user's mouth to the user's ear, the device comprising:
    a signal source configured to produce signals corresponding to sound, music, or instructional material;
    a transducer operatively associated with the signal source to produce vibrations from the signals corresponding to sound, music, or instructional material;
    a sound-transmitting element operatively associated with the transducer to which the transducer can transmit vibrations;
    a power source associated with the signal source;
    a tension controller operatively associated with the transducer to adjust the volume of the produced signal based on the pressure applied by the device to the user's mouth;
    a housing;
    an independent-selective-activity structure, associated with the sound-transmitting element and housing, configured for use in a selectable activity different from denta-mandibular sound transmission;
    where the sound-transmitting element can transmit the vibrations to the user's mouth upon contact of the element with the mouth, so that the vibrations travel from the mouth to the user's ear where they can be perceived by the user as sounds; and
    where the sound-transmitting element is positioned adjacent to the transducer so that vibrations transmitted from the signal source to the sound-transmitting element are sufficient to be perceivable by the user as sound when the sound-transmitting element is in contact with the user's mouth.

2. The device of claim 1, where the independent-selective-activity structure comprises a toothbrush and the selectable activity is practicing good oral hygiene.

3. The device of claim 1, where the signal source comprises a programmable microchip.

4. The device of claim 3, where the programmable microchip comprises an adaptor capable of uploading and downloading data.

5. The device of claim 1, where the sound-transmitting element comprises toothbrush bristles.

6. The device of claim 1, where the transducer comprises an electromagnetic coil assembly and a metal plate.

7. The device of claim 1, where the transducer comprises a piezo-electric crystal.

8. The device of claim 1, where the power source comprises a battery.

9. The device of claim 1, where the power source comprises a series of batteries.

10. The device of claim 1, where the tension controller is selected from the group consisting essentially of a boost switch, a force sensor, a bypass switch, and a limiting resistor.

11. The device of claim 1, where the housing comprises a replaceable head and neck assembly and a handle.

12. The device of claim 11, where the replaceable head and neck assembly comprises the signal source, transducer, and sound-transmitting element.

13. The device of claim 11, where the replaceable head and neck assembly comprises the transducer and sound transmitting element.

14. The device of claim 11, where the handle comprises a motor, gear box, and grip handle to produce a reciprocating action at the toothbrush bristles.

15. A device to communicate sound to a user by the transmission of signals through the user's mouth to the user's ear, the device comprising:
    a signal source configured to produce signals corresponding to sound, music, or instructional material;
    a transducer operatively associated with the signal source to produce vibrations from the signals corresponding to sound, music, or instructional material;
    a sound-transmitting element operatively associated with the transducer to which the transducer can transmit vibrations;
    a power source associated with the signal source;
    a tension controller operatively associated with the transducer to adjust the volume of the produced signal based on the pressure applied by the device to the user's mouth;
    a mechanical lever-pivot;
    a housing; and
    an independent-selective-activity structure, associated with the sound-transmitting element and housing, configured for use in a selectable activity different from denta-mandibular sound transmission;
    where the sound-transmitting element can transmit the vibrations to the user's mouth upon contact of the element with the mouth, so that the vibrations travel from the mouth to the user's ear where they can be perceived by the user as sounds;
    where the mechanical lever-pivot is placed in between the sound-transmitting element and the transducer so that vibrations transmitted from the signal source to the sound-transmitting element are sufficient to be perceivable by the user as sound when the sound-transmitting element is in contact with the user's mouth.

16. The device of claim 15, where the independent-selective-activity structure comprises a toothbrush and the selectable activity is practicing good oral hygiene.

17. The device of claim 15, where the signal source comprises a programmable microchip.

18. The device of claim 17, where the programmable microchip comprises an adaptor capable of uploading and downloading data.

19. The device of claim 15, where the sound-transmitting element comprises toothbrush bristles.

20. The device of claim 15, where the transducer comprises an electromagnetic coil assembly and a metal plate.

21. The device of claim 15, where the transducer comprises a piezo-electric crystal.

22. The device of claim 15, where the tension controller comprises a torsion bar.

23. The device of claim 15, where the tension controller is selected from the group consisting essentially of a boost switch, a force sensor, a bypass switch, and a limiting resistor.

24. The device of claim 15, where the housing comprises a head and neck assembly and a handle, wherein the head and neck assembly comprises the sound-transmitting element.

25. The device of claim 15, where the housing comprises a head and neck assembly and a handle, wherein the handle comprises the power source, source signal, and transducer.

26. A toothbrush device for communicating sound to a user by the transmission of sound signals, the device comprising:
- a toothbrush housing comprising a brush head assembly;
- a signal source configured to produce signals corresponding to sound, music, or instructional material;
- a transducer in the brush head assembly operatively associated with the signal source to produce vibrations from the signals corresponding to sound, music, or instructional material inside the mouth of the user;
- a power source associated with the signal source; and
- a tension controller comprising a flex joint associated with the transducer to switch with pressure applied by the device to the user's mouth to change the volume of the produced signal.

27. The device of claim 26, where the independent-selective-activity structure comprises a toothbrush and the selectable activity is practicing good oral hygiene.

28. The device of claim 26, comprising a sound-transmitting element operatively associated with the transducer to which the transducer can transmit vibrations.

29. The device of claim 26, where the tension controller operatively associated with the transducer to approximate the pressure applied by the device to the user's mouth and to adjust the volume of the produced signal based on the pressure applied by the device to the user's mouth.

30. The device of claim 26, where the sound-transmitting element can transmit the vibrations in the user's mouth so the sound travel from the mouth to the user's ear, and where the mechanical lever-pivot is placed in between the sound-transmitting element and the transducer so that vibrations transmitted from the signal source to the sound-transmitting element are sufficient to be perceivable by the user as sound when the transducer is in the user's mouth.

31. The device of claim 26, where the signal source comprises a programmable microchip.

32. The device of claim 31, where the programmable microchip comprises an adaptor capable of uploading and downloading data.

33. The device of claim 26, where the tension controller is selected from the group consisting essentially of a boost switch, a force sensor, a bypass switch, and a limiting resistor.

34. The device of claim 26, where the housing comprises a head and neck assembly and a handle, wherein the handle comprises the source signal and tension controller.

35. A method for adjusting the volume of a sound in a device to communicate the sound to a user by the transmission of vibrations through the user's teeth, the method comprises the following operations:
- using a tension controller to determine the amount of pressure applied by the device to the user's mouth; and
- adjusting the volume of the sound produces by the device in response to the amount of pressure applied by the device to the user's mouth as to promote proper brushing technique.

36. A method as described in claim 35, where adjusting the volume of the sound produces by the device in response to the amount of pressure applied by the device to the user's mouth as to promote proper brushing technique comprises a torsion bar to control the gap spacing between an electromagnetic coil and a metal plate in a transducer.

37. A method as described in claim 35, where adjusting the volume of the sound produces by the device in response to the amount of pressure applied by the device to the user's mouth as to promote proper brushing technique comprises a diaphragm to control the gap spacing between an electromagnetic coil and a plate in a transducer.

38. A method as described in claim 35, where adjusting the volume of the sound produces by the device in response to the amount of pressure applied by the device to the user's mouth as to promote proper brushing technique comprises a spring to control the gap spacing between an electromagnetic coil and a plate in a transducer.

39. A method as described in claim 35, where adjusting the volume of the sound produces by the device in response to the amount of pressure applied by the device to the user's mouth as to promote proper brushing technique comprises a bellows assembly to control the gap spacing between an electromagnetic coil and a plate in a transducer.

40. A method as described in claim 35, where using a tension controller to determine the amount of pressure applied by the device to the user's mouth comprises of a flex joint located between a head and neck assembly and a handle in which the flex joint activates a switch as the head and neck assembly applies sufficient pressure to the user's mouth.

41. A method as described in claim 35, where adjusting the volume of the sound produces by the device in response to the amount of pressure applied by the device to the user's mouth as to promote proper brushing technique comprises a boost switch that provides an activation signal to a signal source.

42. A method as described in claim 35, where adjusting the volume of the sound produces by the device in response to the amount of pressure applied by the device to the user's mouth as to promote proper brushing technique comprises a bypass switch and a limiting resistor that provides an activation signal to a signal source.

43. A method as described in claim 35, where adjusting the volume of the sound produces by the device in response to the amount of pressure applied by the device to the user's mouth as to promote proper brushing technique comprises a force sensor that provides an activation signal to a signal source.

44. A device to communicate sound to a user by the transmission of signals to the user's ear, the device comprising:
- a signal source configured to produce signals corresponding to sound, music, or instructional material;
- a transducer operatively associated with the signal source to produce vibrations from the signals corresponding to sound, music, or instructional material, comprising a sound-transmitting element operatively associated with the transducer to which the transducer can transmit vibrations in the user's mouth;
- a power source associated with the signal source;
- a tension controller operatively associated with the transducer to adjust the volume of the produced signal based on the pressure applied by the device to the user's mouth;
- a housing;
- an independent-selective-activity structure, associated with the sound-transmitting element and housing, configured for use in a selectable activity different from denta-mandibular sound transmission;
- where the sound-transmitting element is positioned adjacent to the transducer so that vibrations transmitted from the signal source to the sound-transmitting element are sufficient to be perceivable by the user as sound when the sound-transmitting element is in contact with the user's non-sound conductive tissue; and
- where the tension controller operatively associated with the transducer to approximate the pressure applied by the device to the user's mouth and to adjust the volume of the produced signal based on the pressure applied by the device to the user's mouth.

45. The device of claim 44, comprising a sound-transmitting element operatively associated with the transducer to which the transducer can transmit vibrations.

46. The device of claim 44, where the tension controller is selected from the group consisting essentially of a boost switch, a force sensor, a bypass switch, and a limiting resistor.

47. The device of claim 44, where the housing comprises a head and neck assembly and a handle, wherein the handle comprises the source signal and tension controller.

48. The device of claim 44, comprising a mechanical lever-pivot between the sound-transmitting element and the transducer.

49. The device of claim 48, where the sound-transmitting element can transmit the vibrations in the user's mouth so the sound travel from the mouth to the user's ear, and where the mechanical lever-pivot is placed in between the sound-transmitting element and the transducer so that vibrations transmitted from the signal source to the sound-transmitting element are sufficient to be perceivable by the user as sound when the transducer is in the user's mouth.

* * * * *